(12) United States Patent
Dick et al.

(10) Patent No.: US 6,353,150 B1
(45) Date of Patent: Mar. 5, 2002

(54) CHIMERIC MAMMALS WITH HUMAN HEMATOPOIETIC CELLS

(75) Inventors: John E. Dick, Toronto (CA); Douglas E. Williams, Redmond, WA (US); Tsvee Lapidot, Toronto (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 07/797,493

(22) Filed: Nov. 22, 1991

(51) Int. Cl.[7] .................. A01K 67/00; A01K 67/033; C12N 15/63; C12N 15/85
(52) U.S. Cl. .................. 800/8; 435/455; 424/577
(58) Field of Search .............. 800/2, DIG. 2, 800/8; 424/577, 93 U; 435/455

(56) References Cited

FOREIGN PATENT DOCUMENTS

EP 0438053 7/1991

OTHER PUBLICATIONS

Pollard, Tokai J. Exp. Clin. Med. 10(2,3):175–179 (1985).*
Wade et al., Transplantation 44(1) :88–92 (1987).*
Foblmeister et al., Nat. Immun.Cell Growth Regul. 4 :221–228 (1985).*
Kohler et al., "Continuous cultures of fused cells secreting antibody of predifined specificity" *Nature* 256:495–497 (Aug. 7, 1975).
Namikawa et al., "Infection of the SCID–hu Mouse by HIV–1" *Science* 242:1684 (1988). [Namikawa et al. I].
Namikawa et al., "Long–Term Human Hematopoiesis in the SCID–hu Mouse" *J. Exp. Med.*. 172:1055 (1990) . [Namikawa et al. II].
Krowka et al., "Human T Cells in the SCID–hu Mouse are Phenotypically Normal and Functionally Competent", *J. Immunol.* 146:3751 (1991) .
McCune et al., "The SCID–hu Mouse: Murine Model for the Analysis of Human Hematolymphoid Differentiation and Function", *Science 241*:1632 (1988).
Flexner et al., "Successful Vaccination with a Polyvalent Live Vector Despite Existing Immunity to an Expressed Antigen", *Nature 335*:259 (1988) .
Lubin et al., "Engraftment and Development of Human T and B Cells in Mice After Bone Marrow Tranplantation", *Science 252*:427 (1991) .
Kamel–Reid and Dick, "Engraftment of Immune–Deficit Mice with Human Hematopoietic Stem Cells" *Science 242*:1706 (1988) .

* cited by examiner

*Primary Examiner*—Deborah J. R. Clark
*Assistant Examiner*—Peter Paras, Jr.
(74) *Attorney, Agent, or Firm*—Stuart D. Howe

(57) ABSTRACT

There is disclosed a chimeric mammal having a stable bone marrow graft of human hematopoietic cells capable of differentiating into multiple lineages of human mature cells, wherein at least 30% of the hematopoietic cells in the mammal's bone marrow are of human origin. The inventive method comprises sublethally irradiating an immunodeficient mammal, infusing human hematopoietic cells into the mammal and administering an effective amount of human mast cell growth factor (MGF) and a human granulocyte macrophage colony stimulating factor/interleukin-3 fusion protein (GM-CSF/IL-3 FP) to promote engraftment of human cells within the chimeric mammal's bone marrow.

5 Claims, No Drawings

CHIMERIC MAMMALS WITH HUMAN HEMATOPOIETIC CELLS

TECHNICAL FIELD OF THE INVENTION

The present invention relates to a method for engrafting human hematopoietic cells in a non-human mammal by bone marrow transplantation. More particularly, the present invention relates to chimeric mammals with human hematopoietic cells, including progenitor cells and mature cells of the myeloid, lymphoid and erythroid lineages, a process for engrafting human hematopoietic cells to create a chimeric mammal, and a process for creating hybridoma cells capable of producing a human monoclonal antibody.

BACKGROUND OF THE INVENTION

The mammalian hematopoietic system is arranged as a hierarchy consisting of a wide array of cells ranging from large numbers of mature differentiated cells to rare pluripotent stem cells capable of self-renewal and differentiation. Much of our knowledge concerning organization and regulation of mammalian hematopoietic systems is derived from studies with murine hematopoietic systems. Conversely, our understanding of specifics of the human hematopoietic system is much less complete due to a lack of a reliable model for human hematopoiesis. Therefore, there is a need in the art for a human-specific hematopoiesis model that includes human stem cells.

Various investigators have attempted to transplant human hematopoietic cells into a murine bone marrow microenvironment with varying degrees of success. Xenogeneic bone marrow transplantation is possible between closely related species, such as rat and mouse. However, xenogeneic bone marrow transplantation has not enabled the stable transplant of human hematopoietic cells of multiple lineages into more distantly related mammalian species, such as mice or rats. For example, engraftment of human cells in severe combined immune deficiency (SCID) mice, permitted infection of mice with human immunodeficiency virus (HIV) (Namikawa et al., *J. Exp. Med.* 172:1055, 1990). However, detectable human cells were limited to a human T cell lineage and survived for only two to three months. Further, the T cells were detected only in blood and not in any other organ. Thus, transplantation of human hematopoietic cells into SCID mice was limited to the transient survival of only one lineage of human hematopoietic cells.

McCune et al. (*Science* 241:1632, 1988) attempted to facilitate engraftment of human hematopoietic cells (from human fetal liver) into a SCID mouse by further transplanting a graft of human fetal thymic epithelium under the kidney capsule. Control SCID mice that were tansplanted with human hematopoietic cells but not fetal thymic epithelium did not engraft or differentiate into human T cells. No other human cell lineage except human T cells were detected in the mouse tissues. Thus, it appears that transplanted human hematopoiesis observed by McCune et al. occurred only in implanted human thymic tissue and that no engraftment of human cells in murine tissue actually occurred.

EP-A438053 describes an attempt to create a mouse-human chimeric animal. Bone marrow cells from SCID mice and human bone marrow cells were added to another strain of mouse that was lethally irradiated. SCID mouse bone marrow was used because T and B lymphocytic lineages in SCID mice cannot develop from SCID pluripotent stem cells due to a deficiency in rearrangement of antigen receptor genes (Shuler et al., *Cell* 46:963, 1986). The resulting chimeric mice had a small number of human cells in the thymus with a predominant $CD3^+$ $CD4^+$ $CD8^+$ phenotype. Lubin et al. *Science* 252:427, 1991 cotransplanted a T cell depleted human bone marrow with SCID bone marrow into lethally irradiated Balb/c mice. Lubin et al. found only T cells and B cells in blood over several months. Therefore, this procedure did not produce multilineage engraftment of human hematopoietic cells.

Kamel-Reid et al. (*Science* 242:1706, 1988) report the engraftment of human bone marrow cells into SCID mice without implantation of fetal tissue. However, observation periods were limited to thirty days, so long term engraftment was not determined.

Therefore, recent progress to establish a stable chimeric animal model to characterize normal development of human hematopoietic stem cells has been limited to transient or incidental engraftment of one or two human lineages. A chimeric mouse with a high proportion (i.e., predominance) of human hematopoietic cells has not yet been achieved. Such a chimeric mammal would be useful as an experimental model for studying a variety of human and veterinary diseases. Such a chimeric mammal would also be useful for studying normal human hematopoiesis, human stem cells and all of their progeny and those growth and inhibitory factors that govern hematopoiesis. Further, a chimeric mammal with functioning human immune cells would be useful to produce human monoclonal antibodies. The present invention was made to improve techniques used to produce chimeric mammals with human hematopoietic cells.

SUMMARY OF THE INVENTION

The present invention provides a chimeric mammal having a stable bone marrow graft of human hematopoietic cells capable of differentiating into multiple lineages of mature human cells, wherein at least 30% of the hematopoietic cells in the mammal's bone marrow are of human origin. The chimeric mammal is preferably a mouse, and most preferably a SCID mouse. Further, the graft consists essentially of human hematopoietic progenitor cells, multipotent human progenitor cells and mature human hematopoietic cells of lymphoid, myeloid and erythroid lineages.

The inventive method comprises sublethally irradiating an immunodeficient mammal, infusing human hematopoietic cells into the mammal and administering an effective amount of human mast cell growth factor (MGF) and a human granulocyte macrophage colony stimulating factor/interleukin-3 fusion protein (GM-CSF/IL-3 FP) to promote engraftment of human hematopoietic cells. Preferably, GM-CSF/IL-3 FP is a specific fusion protein called PIXY321.

The present invention further provides a chimeric mammal having a stable bone marrow graft of lineage-specific human hematopoietic cells, wherein the lineage-specific human hematopoietic cells are selected from the group consisting of erythroid cells, myeloid cells, lymphoid cells, multipotent progenitor cells and combinations thereof. A process for obtaining a chimeric mammal having a stable bone marrow graft of lineage-specific human hematopoietic cells comprises, sublethally irradiating an immunodeficient mammal, infusing human hematopoietic cells into the immunodeficient mammal, and administering MGF, a GM-CSF/IL-3 FP and an additional, lineage-specific human growth factor which is effective to promote differentiation and proliferation of the desired lineage of human hematopoietic cells. Additional, lineage-specific human growth factors are selected from the group consisting of erythropoietin (EPO), granulocyte-colony stimulating factor (G-CSF), granulocyte macrophage-colony stimulating factor (GM-CSF), macrophage-colony stimulating factor (M-CSF), interleukins-2, -4, -5, -6, -7, -9, -10, -11, and -12, and combinations thereof.

Further still, the present invention provides a human hybridoma cell capable of producing a human monoclonal antibody (hMAb) specific for a selected antigen. The human hybridoma cell is made by a process comprising immunizing a chimeric mammal made according to the inventive process, fusing spleen cells from the chimeric mammal with myeloma cells to make hybridoma cells, and selecting for hybridoma cells which secrete hMAbs that bind to the antigen.

DETAILED DESCRIPTION OF THE INVENTION

The present invention involves various methods of using MGF and a GM-CSF/IL3 FP, such as PIXY321, to promote engraftment of transplanted human hematopoietic cells into various mammalian species. We have significantly improved upon previous methods to create a human-chimeric mammal having at least 30% human cells in the chimeric mammal's bone marrow. Quite often, the proportion of human origin cells versus host mammal hematopoietic cells in the chimeric mammal bone marrow often exceeds 40% or 50% human cells. This level (i.e., at least 30%) of human origin cells of multiple lineages has never been achieved before the present invention. Further, such human cells are capable of differentiating into multiple lineages of mature human cells, such as myeloid, lymphoid and erythroid lineages.

The inventive method involves sublethally irradiating an immunodeficient mammal, such as a SCID mouse, transplanting immature human hematopoietic cells (i.e., from bone marrow, cord blood or peripheral blood), and administering a human engraftment growth factor composition, comprising at least MGF and and a GM-CSF/IL-3 FP, such as PIXY321. The improvement in the inventive method that achieves stable and long-term transplantation of multiple lineages of human hematopoietic cells is administration of an engraftment growth factor composition comprising human-specific cytokines. Preferably, the engraftment growth factor composition is administered by injection (i.e., intraperitoneal, intravenous, subcutaneous, etc) and at least thrice weekly for at least two weeks.

Most preferably, the engraftment composition further comprises an additional, lineage-specific, human cytokine to stimulate proliferation of one or more specific lineages of human hematopoietic cells, wherein the additional, lineage-specific, human cytokine is selected from the group consisting of interleukin-7 (IL-7), granulocyte-colony stimulating factor (G-CSF), granulocyte macrophage-colony stimulating factor (GM-CSF), macrophage-colony stimulating factor (M-CSF), interleukin-1 (IL-1α or IL-1β), interleukin-2 (IL-2), erythropoietin (EPO), interleukin-5 (IL-5), interleukin-4 (IL-4), interleukin-6 (IL-6), and combinations thereof. The additional human cytokine promotes proliferation of more mature or differentiated human myeloid, erythroid, or lymphoid lineage hematopoietic cells.

The present invention further provides a method for preparing a human monoclonal antibody (hMAb) in the inventive chimeric mammal. The hMAb is prepared by first immunizing a chimeric mammal with a selected antigen. Spleen cells from the immunized chimeric mammal are collected and fused with myeloma cells to form hybridoma cells. Human MAbs from supernatants of hybridoma cell cultures are assayed to select hMABs that bind to the selected antigen.

Further still, the present invention provides a chimeric mammal capable of providing a renewable supply of mature human blood cells, such as erythrocytes, monocytes, granulocytes or lymphocytes. The chimeric mammal is made according to the present invention utilizing a human growth factor composition supplemented with a lineage-specific human growth factor. The addition of the lineage-specific growth factor will selectively augment proliferation of a specific lineage of human cell to promote proliferation and differentiation of mature human cells of the specific lineage. Examples of lineage-specific human growth factors include EPO for erythrocytes, G-CSF for neutrophils, IL-2, IL-7, IL-9 or IL-10 for T cells, IL4, IL-6 or IL-7 for B cells, IL-5 for eosinophils and GM-CSF or M-CSF for monocytes.

Chimeric mammals, according to the present invention, are useful for models of human disease, particularly, thalassemia where such chimeric mammals (transplanted with human bone marrow cells from a patient with such a disease) would be useful for preclinical assessment of various treatments. Moreover, chimeric mammals (particularly rats or mice) with a high percentage of human cells in bone marrow (i.e., at least 30%) would be further useful to support human tumor cell growth and serve as a specific model for human leukemia. Lastly larger chimeric mammals (e.g., sheep) can be used as a source of lineage specific cells, such as human erythrocytes when an additional, lineage-specific growth factor is used.

In a preferred method for engrafting human hematopoietic progenitor cells into a living mammal, the inventive process comprises first irradiating an immunodeficient mammal with a sub-lethal dose of irradiation. An immunodeficient mammal, as defined herein, is a mammal that lacks a significant population of functioning, host-specific, T cells and B cells. One example of an immunodeficient mammal is a SCID mouse. A SCID mouse is described, for example, in Kamel-Reid et al., supra. Other examples of immunodeficient mammals include nude, beige, xid (X-linked immune deficiency), and nod (non-obese diabetic) mice. A sub-lethal dose of irradiation is, for example, from about 1000 to about 100,000 rads of radiation per kilogram body weight of the immunodeficient mammal.

The next step involves infusing from about $10^6$ to about $10^9$ human hematopoietic cells per kilogram body weight to the immunodeficient, irradiated mammal. Human hematopoietic cells can be obtained from human bone marrow or human peripheral blood progenitor cells by standard techniques. Human hematopoietic cells (i.e., mononuclear cells) can be separated from bone marrow or peripheral blood, for example, by density gradient sedimentation (e.g., Ficoll).

Engraftment of the human hematopoietic cells from bone marrow or peripheral blood is promoted by administering an effective amount of an engraftment growth factor composition wherein said engraftment growth factor composition comprises hMGF and GM-CSF/IL-3 FP. Preferably, the GM-CSF/IL3 FP is PIXY321. The engraftment growth factor composition is administered at least thrice weekly (by intravenous, intraperitoneal, subcutaneous, intramuscular or other means of systemic administration) for at least two weeks. The engraftment growth factor composition should be administered within one month after administering human hematopoietic cells. Preferably, the engraftment growth factor composition is administered daily for at least one month immediately following human hematopoietic progenitor cell administration. Every other day or thrice weekly administration of the engraftment growth factor composition can also be effective. Most preferably, administration of the engraftment growth factor composition begins immediately after transplantation with human bone marrow.

Mast cell growth factor (MGF) has also been called Steel factor (SF), stem cell factor (SCF), and Kit Ligand (KL). All of the names for this factor refer to the ligand for the c kit proto-oncogene. MGF has been described in a series of seven papers in the Oct. 5, 1990 issue of Cell (Williams et al., Cell 63:167, 1990; Copeland et al., Cell 63:175, 1990; Flanagan and Leder, Cell 63:185, 1990; Zsebo et al., Cell 63:195, 1990; Martin et al., Cell 63:203, 1990; Zsebo et al., Cell 63:213, 1990; Huang et al., Cell 63:225, 1990; and Anderson et al., Cell 63:235, 1990). Expression of various recombinant forms of MGF has been described in U.S. patent application Ser. No. 07/586,073, filed Sep. 21, 1990 and U.S. patent application Ser. No. 07/713,715 filed Jun. 12, 1991, the disclosures of which are incorporated by reference herein. MGF has been found to stimulate proliferation and recruitment of early myeloid and lymphoid lineage progenitor cells and possibly even the most primitive hematopoietic stem cells. Effective amounts of hMGF are from about 100 to about 10,000 µg per kilogram per day.

Fusion proteins comprising GM-CSF and IL-3 components are described in U.S. patent application Ser. No. 07/567,983 filed Oct. 14, 1990, the disclosure of which is incorporated by reference herein. A particular GM-CSF/IL-3 fusion protein (PIXY321) has been found to interact with GM-CSF receptors and/or IL-3 receptors (Curtis et al., Proc. Natl. Acad. Sci. USA 88:5809, 1991). PIXY321 is a GM-CSF/IL-3 fusion protein having $Leu^{23}$ $Asp^{27}$ $Glu^{34}$ $hGM\text{-}CSF/Gly_4$ Ser $Gly_5$ Ser/$Pro^8$ $Asp^{15}$ $Asp^{70}$ hIL-3. Thus, this protein comprises a triply-substituted GM-CSF domain fused to a doubly-substituted $Pro^8$ IL-3 domain via a linker or spacer domain comprising glycine and serine residues. A preferred dose of GM-CSF/IL3 FP or PIXY321 is from about 25 to about 2,500 µg per kilogram per day.

Additional, lineage-specific human cytokines are known in the art and described in various publications. More specifically, interleukin-1 has been found to exist in two forms, IL-1α and IL-1β (March et al., Nature 315:641, 1985). Both IL-1α and IL1β bind to IL-1 receptors (Type I and Type II) to transduce signal. Il-1α is active in both precursor and mature forms, whereas IL-1β is only active in mature form but not in precursor form (March et al., supra). Il-1 also includes active fragments and analogs with altered amino acid sequences and derivatives, such as fusion proteins having an IL-1 component and IL-1 biological activity (Mosley et al., Proc. Natl. Acad. Sci. USA 84:4572, 1987). An appropriate dose for IL-1 is from 50 to 5,000 ng/kg/day.

Interleukin-2 has been described in U.S. Pat. No. 4,738,927, EPO has been described in U.S. Pat. No. 4,703,008, interleukin-7 has been described in U.S. Pat. No. 4,965,195, interleukin-4 has been described in U.S. Pat. No. 5,017,691, interleukins-5 and -6 have been described in Campbell et al., Proc. Natl. Acad. Sci. USA 84:6629, 1987 and Chiu et al., Proc. Natl. Acad. Sci. USA 85:7099, 1988, respectively. Interleukins-9 and -10 have been described in Yang et al., Blood 74:1880, 1989 and Vieira et al., Proc. Natl. Acad. Sci. USA 88:1172, 1991, respectively. Interleukins -11 and -12 have been described in Paul et al., Proc. Natl. Acad. Sci. USA 87:7512, 1990 and Gubler et al., Proc. Natl. Acad. Sci. USA 88:4143, 1991, respectively. Appropriate doses for interleukins-2, -4, -5, -6, -7, -9, -10, -11 and -12 are from 50 to 10,000 ng/kg/day. An appropriate dose range for EPO is from 10 to 1,000 U/kg/day. G-CSF and M-CSF are described in U.S. Pat. No. 4,810,643 and Wong et al., Science 235:1504, 1987, respectively, and an appropriate dose for both is from about 50 to about 10,000 vg/kg/day.

A preferred method for making a hybridoma cell line that secretes a human monoclonal antibody is to inject a chimeric mammal, according to the present invention, with a selected antigen. Preferably, the chimeric mammal is a mouse and most preferably a SCID mouse. Preferably, there are four intraperitoneal injections, approximately one week apart, with about 10 µg of antigen per injection in an adjuvant, preferably Freund's adjuvant. After inoculation the mammals are tested for antibody levels in a test bleeding. Antibody secreting mammals have their spleens removed. Spleen cells are fused with myeloma cells. Suitable myeloma cells include, for example, AG8.653, NS1, and NS0. Hybridoma cells are formed with this fusion.

The hybridoma cells secrete monoclonal antibodies into a culture supernatant. Supernatants are screened for human monoclonal antibodies (hMAb) that both bind to the antigen and are human antibodies. Such screening can be performed in one step. For example, a 96 well plate can be coated with an anti-human rabbit immunoglobulin, and supernatant from the hybridoma cells and labelled antigen added. After washing, only antibodies that are both human and bind to the antigen will form a detectable sandwich within the well. Such hMAbs are selected from this detection.

The present invention is directed to a chimeric mammal. The chimeric mammal is created by employing intravenous (iv) injection of adult human bone marrow into immunodeficient mice conditioned with radiation. Conditioning helps to suppress rejection mechanisms and to promote stem cell engraftment. In earlier attempts to create a chimeric mouse, human macropage cells and their macrophage precursors accumulated in murine bone marrow, increased in number (although nowhere near the percentage of human cells detected according to the present invention), and were maintained in this environment for several months, (Kamel-Reid et al., supra). However, no mature cells were detected (Id.). This procedure was refined in Lubin et al., supra. Therefore, the present invention describes an improved procedure to promote engraftment of human hematopoietic cells of multiple lineages, including granulocytes, macrophages, B cells, erythroid, and multilineage progenitor cells into a non-human mammal (e.g., murine) microenvironment. This supports long term proliferation and differentiation of human hematopoietic stem cells and pluripotent precursor cells of many lineages.

We conducted experiments with sub-lethally irradiated SCID mice transplanted with human hematopoietic cells, found that administration of human engraftment growth factors MGF and PIXY321 (a GM-CSF/IL-3 FP) promotes repopulation of murine bone marrow with human hematopoietic progenitor cells and human mature cells of myeloid, lymphoid and erythroid lineages. When EPO was administered as an additional, lineage-specific human growth factor, mature human red blood cells (HRBC) appeared in the blood of the mice after 30 days of human engraftment growth factor and additional, lineage-specific growth factor administration.

In a group of experiments, SCID mice were sub-lethally irradiated with, for example, 400 cGy, $^{137}$Cs. A lethal dose for a relatively small mouse, such as a SCID mouse, would be at least 500 cGy. Human bone marrow cells from normal volunteers were purified over a density gradient (e.g., Ficoll, Pharmacia) and injected into the sublethally irradiated SCID mice by tail vein injection (i.v.). The mice were administered (i.p.) a human engraftment growth factors composition (PIXY321 @ 8 µg/mouse/2days and MGF @ 20 µg/mouse/2days) every other day for at least two weeks.

The relative amount of human cells in bone marrow of chimeric mammals was determined by sacrificing the mammal (21 to 40 days after human cell infusion), extracting DNA from bone marrow or any other tissue of interest (such as spleen) and analyzing for the presence of human DNA by established procedures. One such procedure for analyzing for human DNA is described in Kamel-Reid et al. *Science* 242:1706, 1988 or Kamel-Reid et al., *Science* 246:1597, 1989. Briefly, DNA was extracted from bone marrow, digested with Eco R1, blotted according to standard procedures, and probed with p17H8 (described in Wave et al., *Nucleic Acids Res.* 15:7549, 1987). p17H8 is a human α-satellite probe specific for sequences on human chromosome 17. Eco R1 digestion of human DNA produces a characteristic 2.7 kb band from human chromosome 17 visible by autoradiography. Autoradiograms were analyzed with a video densitometer (BioRad, Richmond, Calif.) to quantitate 2.7 kb band intensity. Percentage of human cells was determined by comparison to standards with a known percentage of human DNA.

Transplanting human hematopoietic cells into sublethally irradiated SCID mice, without using any growth factors, obtained, at most, up to 2 or 3% human cells in bone marrow. Engraftment growth factor addition dramatically increased the proportion of human cells populating chimeric SCID mouse bone marrow to at least 30% human cells. In a comparative experiment the proportion of SCID mice (sub-lethally irradiated and administered $4 \times 10^7$ human bone marrow mononuclear cells) administered a human engraftment growth factor composition, showed at least a ten fold increase in the level of human cells engrafting in murine bone marrow over those chimeric mice not treated with growth factors. In some mice, the stimulatory effect of a human engraftment growth factor composition exceeded 100-fold. In each experiment, mice receiving human engraftment growth factors, according to the present invention, exhibited levels of human DNA in bone marrow exceeding ten fold the level of human DNA measured in control mice that were not administered human engraftment growth factors. All experiments measured percentage of human cells in bone marrow by determining the intensity of the characteristic 2.7 kb human chromosome 17 α-satellite band in Eco R1-digested DNA. Human/mouse DNA mixtures of known proportions were used as standards.

We determined whether or not human stem cells had engrafted into SCID mice using the inventive procedure. Human stem cells can only be identified indirectly by their function, such as the ability to differentiate into all cell lineages, high degree of self-renewal capacity, slow cell cycling and an ability to engraft for long periods of time. We determined that true human stem cells were able to engraft in a murine bone marrow in chimeric SCID mice produced according to the inventive procedure.

By comparison, when human PBL (peripheral blood lymphocytes, a more mature cell line) were used for transplantation of human cells (instead of human hematopoietic cells from bone marrow or peripheral blood) no human cells were detected in bone marrow of such mice. Therefore, transplantation of mature or more differentiated human lymphoid cells was not responsible for characteristic multilineage engraftment seen in the inventive chimeric mammals. Secondly, continued presence of myeloid and erythroid progenitor cells, and multipotent progenitor cells in the inventive chimeric mammals suggests that earlier precursor cells were able to maintain a pool of human progenitor cells of all lineages. Moreover, we found $CD34^+$ cells in chimeric SCID mice administered an engraftment growth factor composition. This is consistent with a notion that a pool of early progenitor cells had engrafted in bone marrow of inventive chimeric mammals.

In another experiment, SCID mice were transplanted with human bone marrow cells and administration of an engraftment growth factor composition was delayed for one month following transplantation. These mice contained low levels of human myeloid progenitor cells, no detectable erythroid or multilineage progenitor cells, and no detectable mature cells of any lineage at the time the engraftment growth factor composition was administered. One to three months after transplantation, the chimeric mice were administered an engraftment growth factor composition comprising PIXY321 and MGF and, in some instances, a lineage-specific growth factor EPO in addition to the engraftment growth factor composition. High levels of human cells of all lineages were observed in mice receiving the engraftment growth factor composition with or without EPO. Only those mice administered EPO showed detectable BFU-E activity and had significant numbers of $CD19^+$ cells. These data provide evidence that human pluripotent stem cells had engrafted in mouse bone marrow and were responding to human growth factors. These data further suggest that it is possible to select for specific lineages of human hematopoietic cells by administering an additional, lineage-specific human growth factor, such as EPO for erythroid cells.

The following examples are for the purposes of illustration of experimental data using the inventive method.

EXAMPLE 1

This experiment illustrates chimeric mice having at least 30% human cells in its bone marrow. SCID mice were sub-lethally irradiated (400 rads) with $^{137}Cs$. The irradiated SCID mice were maintained under defined flora conditions at the Ontario Cancer Institute. It is preferred to maintain the sub-lethally irradiated mice in a pathogen-free environment Approximately $4 \times 10^7$ human hematopoietic cells from bone marrow of normal volunteers were infused (iv by tail vein) into each irradiated SCID mouse. Seven days after human bone marrow cell transplantation, the mice were administered (intraperitoneally) 8 μg/mouse of PIXY321 and 20 μg/mouse of hMGF every other day for at least 21 to 40 days.

After engraftment growth factor administration, the chimeric mice were sacrificed, DNA was extracted from bone marrow, spleen and thymus and analyzed for presence of human DNA according to a procedure described in Kamel-Reid et al., *Science* 242:1706, 1988 and Kamel-Reid et al., *Science* 246:1597, 1989. Briefly, DNA was extracted from bone marrow, digested with Eco R1, blotted according to standard procedures, and probed with p17H8 (described in Wave et al., *Nucleic Acids Res.* 15:7549, 1987). p17H8 is a human α-satellite probe specific for sequence on human chromosome 17. Eco R1 digestion of human DNA produces a characteristic 2.7 kb band. The intensity of the 2.7 kb band was compared to human/mouse DNA mixtures (0.1%, 1.0% and 10% human). Multiple exposures of the autoradiographs were taken to ensure sensitivity to about 0.01% human DNA.

In one experiment 12 SCID mice were irradiated with 400 cGy, transplanted with about $4 \times 10^7$ human bone marrow cells and administered engraftment growth factors hMGF (20 μg/mouse/2 days) and/or PIXY321 (8 μg/mouse/2 days) or placebo for 40 days (ip every other day). Two mice administered placebo exhibited 0.1% to 1.0% human cells in bone marrow. All four chimeric mice administered engraftment growth factor of both MGF and PIXY321 showed greater than 30% human cells in bone marrow. Chimeric mice administered only PIXY321 as the engraftment growth factor exhibited a greater proportion of human cells than those mice administered MGF alone as the engraftment growth factor. These data illustrate the importance of an engraftment growth factor composition comprising both hMGF and a GM-CSF/IL-3 FP (such as PIXY321) rather than one of the cytokines alone.

In another experiment, we varied the concentration of PIXY321 in the engraftment growth factor composition. The same irradiation and human bone marrow cell transplantation techniques were used. Placebo treated mice exhibited human cell proportions murine bone marrow from <0.01% to about 1.0% depending upon donor human bone marrow. Mice administered a low dose (0.75 µg/day) of PIXY321 showed human cell proportions in the range of the placebo treated mice. Mice administered higher doses (8 µg/2 days) of PIXY321 in the engraftment growth factor composition exhibited proportions of human cells exceeding 10% and often exceeding 30%. The highest proportion of human cells was found in mice administered an engraftment growth factor composition comprising both MGF and higher dose PIXY321.

EXAMPLE 2

This experiment provides a confirmation that immature human bone marrow cells and not mature PBL (peripheral blood lymphocytes) were responding to human growth factor stimulation. In this experiment, a large excess of human peripheral blood lymphocytes ($4 \times 10^7$ cells per mouse) were substituted for human hematopoietic cells in the procedure described in Example 1. This was ten fold more human cells administered to each mouse than the human hematopoietic cells injected in the experiments described in Example 1. Growth factors (placebo, MGF alone, PIXY321 alone, or MGF+PIXY321) were administered ip every other day for 21 or 30 days. No human DNA was detected in murine bone marrow after 30 days of growth factor administration. These data suggest that more primitive, pluripotent human hematopoietic cells were responding to human growth factor stimulation in Example 1, and not mature, differentiated human cells, especially human cells committed to a lymphoid lineage.

EXAMPLE 3

This example illustrates the ability of human hematopoietic cells to engraft and proliferate in a murine microenvironment. Bone marrow cells from chimeric SCID mice ($2 \times 10^5$ cells) administered an engraftment growth factor composition or placebo were assayed in a human progenitor cell assay described in Dick et al., *Blood* 78:624, 1991. A human progenitor cell assay was used to determine human hematopoietic colonies in murine bone marrow by a methylcellulose culture procedure. Briefly, the methylcellulose cultures contained pre-tested lots of human plasma and 10 U/ml human IL-3, 1.0 U/ml human GM-CSF, 5 ng/ml PIXY321, 50 ng/ml MGF and 1 U/ml human EPO. Morphological criteria were used to identify colonies derived from colony-forming units of granulocyte/macrophage (CFU-GM), burst-forming unit erythroid (BFU-E), and colony-forming unit granulocyte/macrophage/erythroid/megakaryocyte (CFU-GEMM) progenitors.

Chimeric mice administered a placebo or various engraftment growth factor compositions were analyzed for total human progenitor cells per $2 \times 10^5$ cells plated in a methylcellulose assay. The following table compares results for human progenitor cells in chimeric mice transplanted identically except administered various combinations of growth factors.

TABLE 1

| Growth Factor | # mice | Mean # human progenitors | Range |
| --- | --- | --- | --- |
| Placebo | 13 | 2 | 0–10 |
| PIXY321 | 8 | 18 | 2–40 |
| MGF + PIXY321 | 7 | 24 | 10–70 |
| MGF + PIXY321 + EPO | 6 | 23 | 0–98 |

In general, administration of human engraftment growth factors resulted in an approximate ten-fold increase in total number of progenitor (BFU-E and CFU-GM) colonies. Most notably, bone marrow from one chimeric mouse (#164-14), administered MGF and PIXY321, had 50 CFU-GM and 26 BFU-E per $2 \times 10^5$ cells plated. Many BFU-E colonies from engraftment growth factor-treated chimeric mice were macroscopic and composed of several small clusters typical of early erythroid progenitors.

Blast colony-forming progenitors colonies detected were confirmed by histological analysis after 21 days of culture. The number of colonies were counted after 8–14 days of incubation. Close inspection of plates from chimeric mouse #164-14, after three weeks of culture, found two small blast colonies. Although these two blast colonies were not tested, some blast colonies have replating potential and may be derived from an early progenitor cell type (Leary and Ogawa, *Blood* 69:953, 1987; Sutherland et al., *Proc. Natl. Acad. Sci. USA* 87:3585, 1990).

More specifically, the following Table 2 illustrates data showing multiple lineages of human hematopoietic cells present in several chimeric mice. The control mice were treated with placebo growth factor and are the averages from 15 control mice.

TABLE 2

| | | progenitor colonies per $2 \times 10^5$ cells plated | | | |
| --- | --- | --- | --- | --- | --- |
| Mouse | Growth Factor (days) | BFU-E | CFU-GM | CFU-GEMM | Blast |
| 164–4 | MGF + PIXY (>30) | 26 | 50 | 0 | 2 |
| 167–15 | PIXY (>30) | 8 | 20 | 0 | 0 |
| 178–4 | PIXY + EPO (30–>60) | 58 | 50 | 6 | 0 |
| 181–8 | PIXY + EPO (30–>60) | 23 | 101 | 0 | 1 |
| Control | none | 0 | 3 | 0 | 0 |

These results establish that chimeric mice administered engraftment growth factors, according to the present invention, comprise human hematopoietic progenitor cells committed to myeloid and erythroid lineages, and occasionally an earlier multipotential progenitor cell. Moreover, the number of such human hematopoietic progenitor cells are significantly higher in chimeric mice administered an engraftment growth factor composition, according to the present invention, than those mice administered a placebo. These data further suggest the importance of a combination of a GM-CSF/IL-3 FP, such as PIXY321, and MGF as a human engraftment growth factor composition to achieve the highest proportion of human cells in a chimeric mammal bone marrow.

EXAMPLE 4

This example provides data to further support the utility of the inventive chimeric mammals transplanted with human bone marrow cells and receiving appropriate human growth factors. More particularly, this example provides data showing continuous production of human antibodies in inventive chimeric mammals. The half life of human immunoglobulins is less than five days in SCID mice (Saxon et al., *J. Clin. Invest.* 87:658, 1991). Therefore, persistence of human immunoglobulin in SCID mice for 30–60 days indicates continuous production of Ig by human B cells.

Human IgG and IgM were measured in plasma from chimeric mammals using an automated Particle Florescence Immunoassay procedure (PCFIA) as described in Dosch et al., *Internat. Immunol.* 2:833, 1990. Briefly, affinity purified goat anti-human IgG and IgM (Calag) were covalently coated onto polystyrene beads (Baxter-Pandex) and added to a unidirectional flow vacuum (Baxter-Pandex). A 1:3 cascade dilution of murine plasma was added and washed automatically. Concentration of bound human immunoglobulin was measured by adding FITC-conjugated affinity purified anti-human goat IgG or IgM antibodies (Jackson Immunoresearch). Fluorescence was determined on a Baxter-Pandex Screen Machine. Each sample was assayed a minimum of six times and compared to a standard curve prepared from purified human IgG or IgM (Sigma, St. Louis). Negative control samples were CID or Balb/c plasma.

Chimeric mice administered PIXY321 and MGF as the engraftment growth factor composition, according to procedures described in Example 1 herein, maintained detectable titers of human IgG and IgM, often in excess of 100 μg/ml of human IgG and 1–30 μg/ml of human IgM. Accordingly, these antibody data are evidence for continuous production of human B cells by inventive chimeric mammals.

EXAMPLE 5

This example provides data supporting a showing that multiple lineages of myeloid, lymphoid and erythroid cells were present in bone marrow of inventive chimeric SCID mice. Bone marrow cells from chimeric SCID mice were incubated with saturating amounts of a conjugated monoclonal antibody specific to human specific antigen CD45 (KC56, Coulter). CD45 is expressed on a majority of human hematopoietic cells. The bone marrow cells from chimeric mammals were also incubated with saturating amounts of conjugated monoclonal antibodies directed against CD35 (10M34, Amac) and CD33 (MY9, Coulter) early myeloid antigens, granulocyte and macrophage antigen CD13 (MY7, Coulter), early B cell antigen CD19 (B4, Coulter), T cell antigen CD3 (T3, Coulter), and glycophorin present on erythroid cells (Amac). Each monoclonal antibody was conjugated to FITC (fluorescein isothiocyanate) or phycoerythrin. Incubated samples were assayed for conjugated antibody by human cell binding on an EPICS Profile Analyzer (Coulter, Hialeah, Fla.). The amount of background staining in a single or double positive window never exceeded 2%, and this amount was subtracted from the percentage staining of positive cells automatically calculated for test samples.

TABLE 3

| Growth Factor (days) | percentage positive cells | | | | |
|---|---|---|---|---|---|
| | CD34 | CD33 | CD13 | CD19 | Glycophorin |
| none (0->30) | 0 | 0 | 0 | 0 | 0 |
| MGF + PIXY (0->30) | 2.2 ± 0.6 n = 6 | 11.8 ± 5.5 n = 3 | 2.8 ± 0.9 n = 6 | 0.9 ± 0.7 n = 9 | 5.5 ± 1.2 n = 2 |
| none (0->60) | 0 | 0 | 0 | 0 | 0 |
| MGF + PIXY (0->30) | nt | 2.9 ± 0.8 n = 5 | 2.9 ± 0.5 n = 3 | 7.3 ± 2.9 n = 9 | nt |

No CD2$^+$ T cells were found in bone marrow from any chimeric mice that were analyzed. Therefore, these data establish that the human engraftment growth factor composition is necessary to promote engraftment of human hematopoietic progenitor cells, particularly of the myeloid, lymphoid, and erythroid lineages.

EXAMPLE 6

This example illustrates the ability of a chimeric SCID mouse to produce lineage-specific cells in response to administration of engraftment growth factors PIXY321 and MGF and an additional, lineage-specific growth factor. EPO was used as the additional, lineage-specific growth factor in this experiment. EPO promoted proliferation of human erythrocytes. Mature human erythrocytes were detected only in mice administered EPO.

Human erythrocytes were detected by two independent methods, agglutination with antibodies directed against the blood group A antigen (when human bone marrow cells were donated by an individual with type A blood) and electrophoretic separation of murine and human hemoglobin. It was possible to detect as little as 1% human erythrocytes in a mixture using an anti-type A agglutination technique and low power microscopy.

Low levels of agglutination (about 1% human erythrocytes) was detected in blood of chimeric mammals administered engraftment growth factors PIXY321 and MGF but not EPO. More extensive agglutination (approximately 5% human erythrocytes) was found in blood from chimeric mammals administered a combination of engraftment growth factors (PIXY321 and MGF) and EPO for thirty days.

Agglutination results were confirmed by measuring amounts of human and murine hemoglobin in blood from chimeric mammals. Human and murine hemoglobin can be distinguished by electrophoretic separation on cellulose acetate plates according to a method described in Whitney, *J. Biochem. Genet.* 16:667, 1978. Two species of murine hemoglobin migrate slower than human hemoglobin. Human hemoglobin levels as low as 2% can be reproducibly detected by this method in mixtures of murine/human erythrocytes.

Blood from chimeric mice administered engraftment growth factors for one month but not EPO were negative for human hemoglobin by this method. When the same mice were administered a triple combination of PIXY321, MGF and EPO for a second month, their blood contained detectable amounts of human erythrocytes (determined by agglutination) and human hemoglobin (determined by electrophoresis). These data suggest that administration of a human engraftment growth factor composition, according to the present invention, supports engraftment of human erythroid precursor cells. These data further suggest that administration of additional, lineage-specific growth factor EPO supports differentiation of the engrafted erythroid precursor cells into mature human red blood cells.

What is claimed is:

1. A chimeric mouse comprising a stable bone marrow graft of human hematopoietic cells, wherein said graft differentiates into multiple lineages of mature human cells and wherein at least 30% of the hematopoietic cells in said bone marrow are of human origin, and wherein said graft is transplanted by a process comprising:
   a. sublethally irradiating an immunodeficient mouse, wherein the immunodeficient mouse lacks a population of functional T cells and B cells;
   b. infusing from about $10^6$ to about $10^9$ human hematopoietic cells into said immunodeficient mouse; and
   c. administering an effective amount of human mast cell growth factor (MGF) and a human granulocyte macrophage colony stimulating factor/Interleukin-3 fusion protein (GM-CSF/IL-3 FP) to promote engraftment of the human hematopoietic cells.

2. The chimeric mouse of claim 1, wherein the graft consists of human hematopoietic progenitor cells, multipotent human progenitor cells, and human hematopoietic cells of the lymphoid, myeloid and erythroid lineages.

3. A process for engrafting human hematopoietic cells into an immunodeficient mouse comprising:
   a. irradiating the immunodeficient mouse with about 5000–10,000 rads/kg body weight;
   b. infusing about $10^6$–$10^9$ human hematopoietic cells per kilogram body weight into said immunodeficient mouse; and
   c. administering an effective amount of MGF and GM-CSF/IL-3 FP to the immunodeficient mouse, that results in promoting stable engraftment of human hematopoietic cells.

4. The process of claim 3, wherein the dose of MGF is about 200–10,000 µg/kg/day and the dose of GM-CSF/IL-3 FP is about 25–2,500 µg/kg/day.

5. The process of claim 3, wherein said GM-CSF/IL-3 FP is PIXY321.

* * * * *